United States Patent
Georgeson et al.

(10) Patent No.: US 6,991,371 B2
(45) Date of Patent: Jan. 31, 2006

(54) COMPUTED TOMOGRAPHY IMAGE QUALITY PHANTOM

(75) Inventors: Gary E. Georgeson, Federal Way, WA (US); James M. Nelson, Sumner, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 67 days.

(21) Appl. No.: 10/685,196

(22) Filed: Oct. 14, 2003

(65) Prior Publication Data

US 2005/0078801 A1    Apr. 14, 2005

(51) Int. Cl.
*G01D 18/00*    (2006.01)

(52) U.S. Cl. .................. 378/207; 378/18; 378/57

(58) Field of Classification Search ............. 378/207, 378/18, 57

See application file for complete search history.

(56) References Cited

U.S. PATENT DOCUMENTS

| | | | | |
|---|---|---|---|---|
| 4,055,771 A | * | 10/1977 | Goodenough et al. | 378/18 |
| 4,344,183 A | * | 8/1982 | Jacobson | 378/207 |
| 6,674,834 B1 | * | 1/2004 | Acharya et al. | 378/18 |
| 6,813,374 B1 | * | 11/2004 | Karimi et al. | 378/207 |
| 2004/0245447 A1 | * | 12/2004 | Karasawa | 378/207 |
| 2005/0025280 A1 | * | 2/2005 | Schulte | 378/57 |

OTHER PUBLICATIONS

QUASAR "Quality Assurance for Radiation Therapy and IMRT-Quasar Phantoms and Vista" http://modusmed.com/quasar-bodyphant-mp.htm (C) 2000, 2001, last accessed Mar. 10, 2005.*

* cited by examiner

*Primary Examiner*—Craig E. Church
*Assistant Examiner*—Krystyna Suchecki
(74) *Attorney, Agent, or Firm*—John A. Artz

(57) ABSTRACT

A computed tomography (CT) image quality phantom for use in calibrating explosive detection systems (EDS) at airports. A foam core block containing up to five right cylinder rod members is positioned in a housing member which is adapted to be passed through an airport luggage scanning machine. The rod members are of different lengths in order to create different data slices for analysis. The housing has a lead-in member at least at one end in order to allow passage through an EDS more easily and provide accurate CT calibrating.

15 Claims, 3 Drawing Sheets

COMPUTED TOMOGRAPHY IMAGE QUALITY PHANTOM

GOVERNMENT INTEREST

This invention was made with Government support under Contract No. DTSA 20-03-C-00002 awarded by TSA for Homeland Security. The Government has certain rights in this invention.

TECHNICAL FIELD

The present invention relates to devices for calibrating computed tomography (CT) systems, and more particularly to devices for verifying the performance of luggage scanner machines at airports.

BACKGROUND OF THE INVENTION

Devices and systems for detecting explosives and other terrorist-type devices are installed in virtually every United States airport. Devices for detecting explosive systems are referred to as Explosive Detection Systems (EDS). These systems are based upon x-ray computed tomography (CT) systems and produce images of x-ray attenuation of the interior of luggage, packages and the like that are reviewed for evidence of hidden explosives. The devices in which the luggage, packages, and other items are passed through are also called "scanners."

There currently are not any standard methodologies or corresponding hardware for evaluating how well an EDS is performing consistently over time. Currently, CT phantoms of various sizes and shapes are used to determine one performance measure or another, at one location or another, in the field of view. There currently are not any devices or systems for measuring performance across the entire field of view of the EDS, nor of determining image resolution and contrast sensitivity quantitatively with a single test phantom.

The standard test method for measuring the performance of computer tomography systems is set forth in American Society for Testing and Materials (ASTM) E1695. This test method provides instruction for determining the spatial resolution and contrast sensitivity in x-ray and γ-ray computed tomography images. The determination is based on examination of the CT image of a uniform disk of material. The spatial resolution measurement is derived from an image analysis of the sharpness at the edge of the disk. The contrast sensitivity measurement is derived from an image analysis of the statistical noise at the center of the disk.

There is a need for a simple and efficient test measuring device and process which can assist in the calibration of EDS systems in a quicker and easier manner, and which provides uniform and accurate results. There also is a need for measuring performance of EDS systems and devices, particularly across the entire field of view and with a single test device.

SUMMARY OF THE INVENTION

The invention provides a shaped exterior housing containing an inner foam core with a plurality of plastic cylinders which are imaged during scanning. The cylinders are right cylinders and positioned uniformly in a foam matrix and positioned in the exterior housing. The right cylinders are of different lengths and preferably five are provided.

The housing with the foam and right cylinders inside are passed through an EDS device where it is scanned in the same manner as any common piece of luggage or other package. The data produced from the scan takes into account the entire field of view. The size and shape of the housing are provided to allow it to pass easily through an EDS and at the same time be sufficiently stable to generate accurate machine measurements.

The existence of attenuating material within the field of view creates image artifacts and ascertains the image resolution and contrast sensitivity simultaneously. Measurements are made at locations from which performance curves are generated. The measurements are based upon ASTM E1695 standards. The results are an ASTM-validated definition of system performance across the entire field of view and includes image resolution and contrast sensitivity measurements.

Use of the present invention allows an operator of an EDS to insure that the system maintains a required level of explosive detection at all times.

DESCRIPTION OF PREFERRED EMBODIMENTS

The present invention was developed to accurately and systematically verify the performance of an x-ray computed tomography (CT)-based explosive detection systems (EDS) in common use at U.S. airports. These EDS systems, which commonly are called "scanners," produce images of x-ray attenuation of the interior of luggage, packages and the like that can be reviewed for evidence of hidden explosives.

Figure 1:
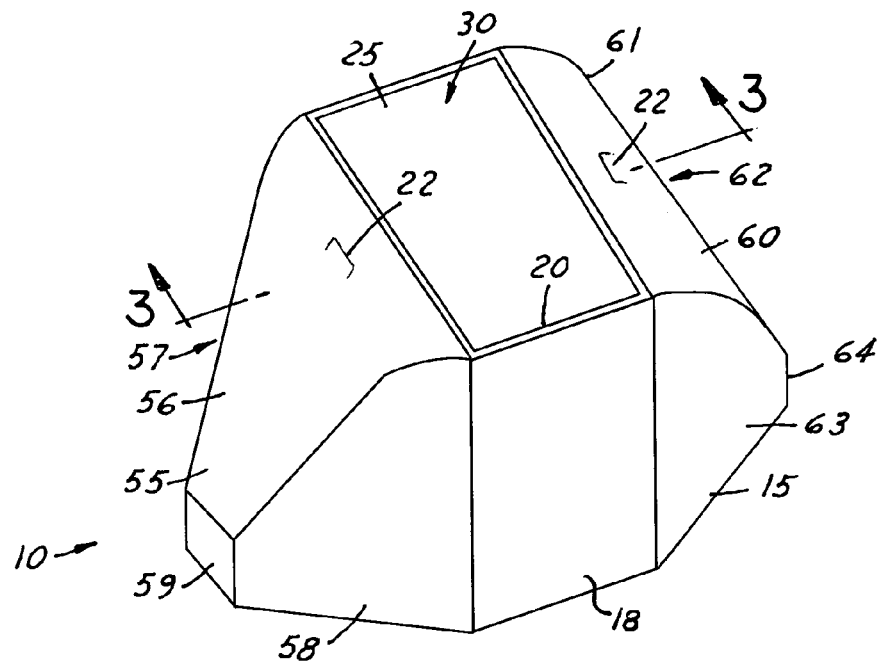
FIG. 1 illustrates a computed tomography image quality phantom in accordance with the present invention.
Figure 2:
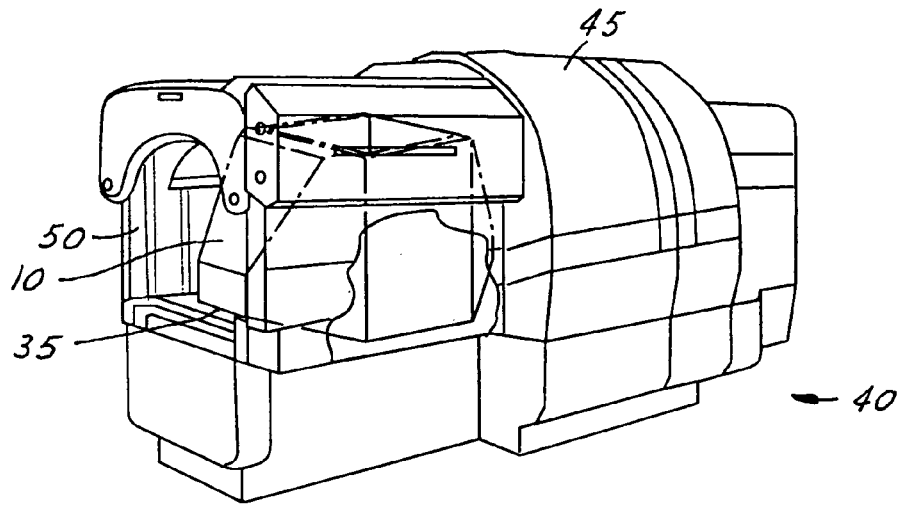
FIG. 2 illustrates the use of a phantom in accordance with the present invention.

As shown in FIG. 1, the phantom 10 is shown in a perspective view and includes an exterior housing 15 which has a recess or cavity 20. A core block 25 is positioned in the cavity or recess 20. In addition, a plate or cover member 30 can be positioned on the housing in order to hold the core block 25 firmly in position in the housing 15.

In use for calibrating EDS machines, the phantom 10 is positioned on the conveyor belt 35 of an airport luggage scanner 40. As is common in airport security systems today, luggage, packages, and other items are positioned on the conveyor belts of the scanning machines and then passed through a housing, such as housing 45, where they are scanned by a CT system. For the protection of the operators, a series of straps of lead-based material 50 are positioned on the entrance and exit of the housing 45. The lead-strips protect the users from stray x-rays.

In order to effectively pass through the housing of the scanner, the phantom 10 has a pair of tapered bull nose end members 55 and 60 which are positioned on opposite sides of the central body member 18 of the housing 15. The bull nose members 55 and 60 have a plurality of slanted side surfaces, which are designated 56, 57 and 58 and 61, 62 and 63, respectively, as well as front lead-in surfaces 59 and 64, respectively. The slanted and lead-in surfaces allow the phantom 10 to pass through the lead strips 50 of the EDS scanner 40 more easily, and also prevent the scanner from moving or turning in any manner as it passes through the measurement area in the housing 45.

In this regard, the phantom 10 should be positioned on the conveyor belt 35 so that it is in alignment with the longitudinal axis of the EDS scanner. In this manner, the right cylinders (described below), which are positioned in the core block 25, are maintained in position along the longitudinal axis and direction of travel through the EDS scanner. This provides the most accurate and precise measurements.

The core block 25 is preferably made from a foam material, particularly low density foam with a low atomic number. Since foam material is mostly air, its density is low, and will have a negligible effect on the x-rays. The material used for the core block, however, also should have sufficient rigidity to support a plurality of rods or cylinders which are used to calibrate the EDS machine.

The exterior structure of the housing 15 should be sufficiently large to cover the entire x-ray field of view of the EDS devices, but small enough to easily pass through the entrances and exits of the EDS devices without being turned, tipped over or becoming stuck. The phantom 10 also should be light enough for one person to carry and position on the conveyor belt, but be durable enough to be used every day.

The housing member 15 can be made of any material but preferably is a plastic material such as ABS. Other conventional plastic materials can be utilized, so long as they do not significantly interfere with the x-ray measurements. The housing 15 can be manufactured in any conventional manner, such as by plastic injection molding techniques.

With the present invention, at least two rod members or cylinders are provided. They are positioned in the core block, one in the center and one adjacent an edge. Preferably, however, five rod members are provided and positioned in the manner shown in FIGS. 4–6. It is also possible to utilize more than five rod members.

Figures 4, 5:
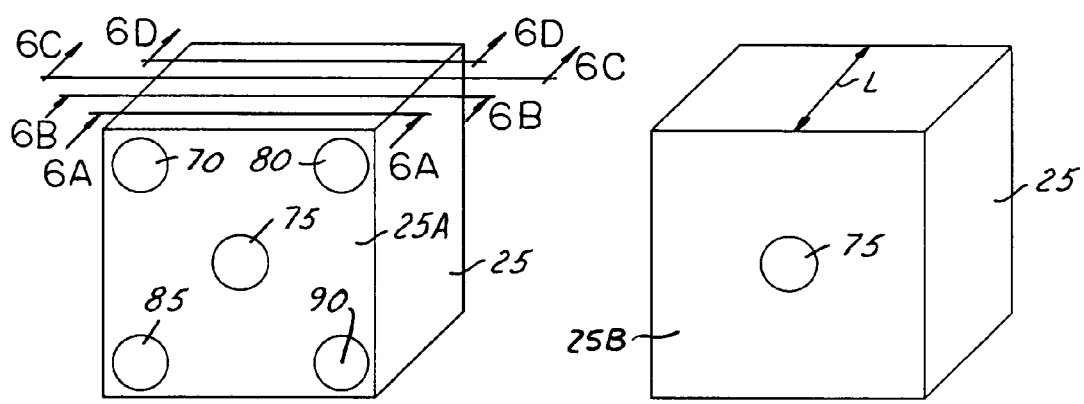
FIG. 4 illustrates a core block for use with the present invention.
FIG. 5 illustrates the opposite side of the core block depicted in FIG. 4.
Figure 6A:
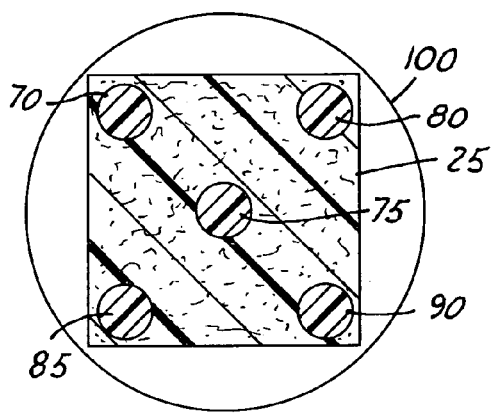
FIGS. 6A–6D are cross-sectional views taken at various distances along the length of the core block as shown in FIG. 4.
Figure 6B:
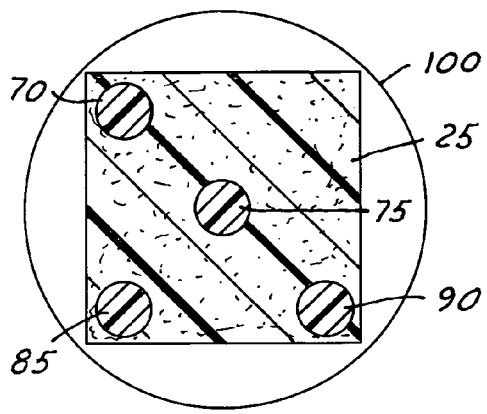
Figure 6C:
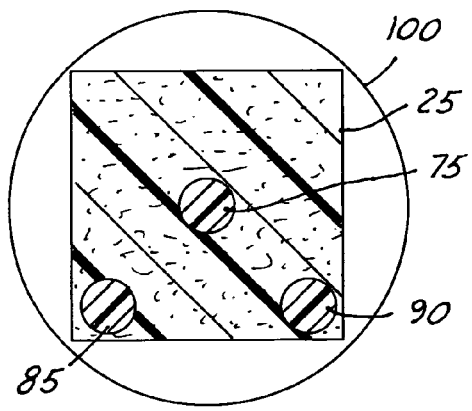
Figure 6D:
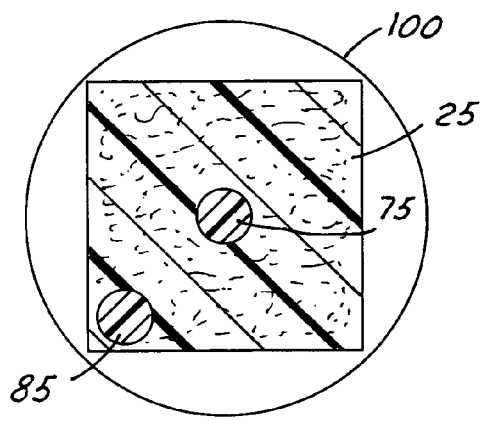

In the preferred embodiment, as shown in FIGS. 4–6, five rod members 70, 75, 80, 85, and 90 are positioned in the core block 25. The rods are preferably made from a plastic material, such as acrylic or DELRIN, which has a density close to the density of explosive materials. In this regard, most explosives are made with gasoline, gun powder, or hydrocarbons of some type and thus the acrylic, DELRIN, or other plastic material used for the rods preferably have a density of the same value.

The rod members are preferably right cylinders of different lengths. For example, as shown in FIGS. 4–6, the rod member 75 positioned in the center of the foam block extends the entire distance from the front surface 25A to the rear surface 25B (see FIG. 5). The remaining four rod members 70, 80, 85 and 90 are positioned in the corners of the foam block as shown. This provides a phantom with the ability to measure the entire field of view or at least as close to possible to the entire field of view of the EDS.

The rod members are typically three-four inches in diameter and about 10–12 inches in length. With five rod members, it is preferable that they be of proportional lengths. For example, the five rod members shown in FIGS. 3–6 could be two inches, four inches, six inches, eight inches, and ten inches in length, with rod member 75 being the longest.

Due to the different lengths of the five rod members, the x-ray slices through the core block at different locations along the length "L" of the foam block (see FIG. 5) will depict various numbers of the rod members. This is shown in cross-sectional slices 6A, 6B, 6C, and 6D. In this embodiment shown, assuming that the centrally located rod member 75 is ten inches in length, then rod member 80 is two inches in length, rod member 70 is four inches in length, rod member 90 is six inches in length, and rod member 85 is eight inches in length.

In order to mount the rod members in the foam block, appropriate openings or holes are formed in the foam block. The openings or holes can be formed in any conventional manner, such as with a hot wire mechanism.

It is desirable to have four of the rod members positioned in the corners of the foam block in order to be as close as possible to the outer diameter of the field of view of the CT scanner. Since the field of view of a CT machine is typically round, as shown by subscribed circle 100 in FIG. 6A, the rod members will be positioned close to the circumference of that circle.

Figure 3:
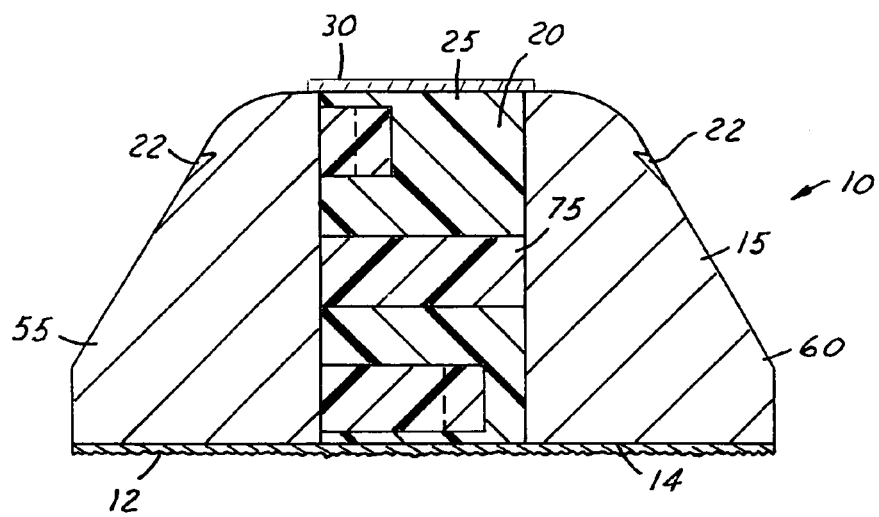
FIG. 3 is a cross-sectional view of the phantom of FIG. 1, the cross-sectional view taken along lines 3—3 in FIG. 1 and in the direction of the arrows.

The phantom 10 preferably has a flat bottom surface 12. The surface 12 also can have a conventional type of tread or anti-slip member or surface 14 thereon, as shown in FIG. 3. This will assist in preventing the phantom from slipping or turning on the conveyor belt 35 as the phantom is passed through the EDS scanner housing.

In order to manually position the phantom 10 on the conveyor belt 35, preferably one or more openings or hand holds 22 are positioned in the housing 15.

It is preferable that EDS systems at airports be calibrated every day. This can be done at the time that the scanner is first energized or activated before it is used to scan luggage and packages of passengers.

With five rod members, it is possible to independently evaluate the performance of the CT scanner over the entire field of view. The data produced from the scan takes into account the entire field of view in this manner.

Although the foam core block 25 is provided with a rectangular solid shape, it is also possible in accordance with the present invention to provide a core structure of a different shape. It is also possible to provide more than five rod members or cylinders.

The measurements taken by the CT machine are preferably based upon the American Society of Testing and Material Standard (ASTM) E1695. Software will enable the cylinders to be analyzed in the slices of CT data that are generated by the EDS. The software will undertake a series of measurements at the cylinder locations and then generate performance curves. The results will be an ASTM-validated definition of system performance across the entire field of view. The results also include important image resolution and contrast sensitivity measurements.

The five rod members or cylinders are used to provide different levels of x-ray attenuation for different data slices. The position and arrangement of rod members as shown in FIGS. 3–6, and if made of material such as acrylic or DELRIN, will represent the range of attenuation that a system will experience at an airport.

The rod members are positioned in space to provide data near the corners of the field of view, as high as possible and as wide as possible, while still having one cylinder near the center of the EDS field of view. This pattern obtains x-ray attenuation from one to five cylinders of material, while maximizing the measurement in the field of view.

The software should automatically assess the CT images taken of the phantom. Software will locate the cylinders in each CT slice and make various measurements on the data at those locations. It then can provide various data curves for CT resolution and contrast sensitivity which define the EDS performance.

Inputs to the software include the radius range for the cylinders included in the calculations and the density of the cylinders. The output preferably is a series of data curves including the following: modulation (%) versus feature size (mm); error in the mean (%) versus feature size (mm); contrast discrimination (%) versus feature size (mm); modulation (%) versus frequency (lines pairs per mm); and response (dimensionless) versus position (mm).

The housing 15 of the phantom 10 in accordance with the present invention can also be used to carry other types of CT phantoms that may be used for system analysis. For example, the core block which is positioned in the housing 15 can be removed and a CT lined pair gage or a CT step wedge can be positioned inside the cavity or recess 20.

While the invention has been described in connection with one or more embodiments, it is to be understood that the specific mechanisms, processes and procedures which have been described are merely illustrative of the principles of the invention, numerous modifications may be made to the methods and apparatus described without departing from the spirit and scope of the invention as defined by the appended claims.

What is claimed is:

1. A device for calibrating a CT machine, said device comprising:
   a housing member adapted to pass through an CT machine;
   a foam core member positioned in said housing, said foam core member having a first surface and an opposite second surface;
   a plurality of cylinder members positioned in said foam core;
   said cylinder members each having a different length and each having a constant cross-section throughout said length;
   each of said cylinder members having a first portion adjacent said first surface; and
   at least one of said cylinder members having a second portion adjacent said second surface.

2. The device as described in claim 1 wherein said CT machine has a field of view and wherein said plurality of cylinder members are uniformly positioned spatially in said foam core member thereby allowing calibration of the CT machine substantially across the entire field of view.

3. The device as described in claim 1 wherein five cylinder members are provided.

4. The device as described in claim 3 wherein said five cylinder members are positioned in a hub-and-spoke type arrangement and said at least one of said cylinder members is positioned substantially in the center of said arrangement.

5. The device as described in claim 1 wherein two cylinder members are provided.

6. The device as described in claim 1 wherein said foam core member has a longitudinal axis and one of said cylinder members is positioned substantially along said longitudinal axis.

7. The device as described in claim 1 wherein said cylinder members are made from a plastic material.

8. The device as described in claim 1 wherein said foam core member has a substantially rectangular cross section and a longitudinal axis, and wherein five cylinder members are provided.

9. The device as described in claim 8 wherein one of said cylinder members is positioned along said longitudinal axis and the other four cylinder members are positioned adjacent the four corners of said rectangular shaped foam core member.

10. The device as described in claim 9 wherein said at least one of said cylinder members which has a first portion adjacent said first surface and a second portion adjacent said second surface is positioned substantially along said longitudinal axis.

11. The device as described in claim 1 wherein said housing member has a recess and said foam core member is positioned in said recess.

12. The device as described in claim 11 further comprising a cover member for enclosing said foam core member in said recess.

13. The device as described in claim 1 wherein said housing member has a lead-in member at least at one end adapted to facilitate passage through said CT machine.

14. The device as described in claim 13 wherein said housing member has a load-in member at two opposing ends.

15. The device as described in claim 1 wherein said foam core member is made from a foam material, and said cylinder members are made from a Delrin™ material.

* * * * *